United States Patent [19]

Spitzer

[11] Patent Number: 4,670,445

[45] Date of Patent: Jun. 2, 1987

[54] INOTROPIC AGENTS

[75] Inventor: Wayne A. Spitzer, Indianapolis, Ind.

[73] Assignee: Eli Lilly and Company, Indianapolis, Ind.

[21] Appl. No.: 797,306

[22] Filed: Nov. 12, 1985

Related U.S. Application Data

[62] Division of Ser. No. 586,361, Mar. 5, 1984, Pat. No. 4,578,387.

[51] Int. Cl.$^4$ ............... C07D 471/04; A61K 31/415
[52] U.S. Cl. ......................................... 514/300; 546/121
[58] Field of Search .................... 546/121; 514/300

[56] References Cited

U.S. PATENT DOCUMENTS

| | | | |
|---|---|---|---|
| 3,494,928 | 2/1970 | Frey et al. | 260/293.4 |
| 3,985,891 | 10/1976 | Kutter et al. | 424/263 |
| 4,141,899 | 2/1979 | Arcari et al. | 546/118 |
| 4,299,834 | 11/1981 | Austel et al. | 424/253 |
| 4,507,481 | 3/1985 | Davidson et al. | 546/121 |
| 4,603,206 | 7/1986 | Davidson et al. | 546/121 |

FOREIGN PATENT DOCUMENTS

| | | | |
|---|---|---|---|
| 647290 | 8/1964 | Belgium | 546/121 |
| 50-108290 | 2/1974 | Japan | 546/121 |
| 479770 | 4/1976 | U.S.S.R. | 546/121 |

OTHER PUBLICATIONS

Biniecki et al., Roczniki Chemii; Ann Soc. Chim. Polonorum, vol. 48, pp. 1595–1598 (1974).
Biniecki et al., Chemical Abstracts, vol. 82, entry 11194q (1975).

*Primary Examiner*—John M. Ford
*Attorney, Agent, or Firm*—Robert A. Conrad; Leroy Whitaker

[57] ABSTRACT

This invention provides for certain phenyl-substituted imidazo compounds, their pharmaceutical formulations, and their use as positive inotropic agents and vasodilators.

13 Claims, No Drawings

INOTROPIC AGENTS

This application is a division of application Ser. No. 586,361, filed Mar. 5, 1984, now U.S. Pat. No. 4,578,387.

BACKGROUND OF THE INVENTION

The cardiac glycosides and the sympathomimetic amines are the principal inotropic agents used in the management of congestive heart failure. Although the cardiac glycosides, especially digitalis, are among the most frequently prescribed drugs, they have numerous liabilities such as a low therapeutic index and erratic absorption, and are associated with life-threatening arrhythmias and deleterious drug-drug interactions. In addition, many patients either do not respond, or become refractory to these agents. The sympathomimetic amines, such as dopamine and epinephrine, have limited utility due to positive chronotropic effects, arrhythmogenic properties, and oral ineffectiveness.

More recently, new classes of inotropic agents have been found. Among these, certain 2-phenylimidazo[4,5-b]pyridines (U.S. Pat. Nos. 3,985,891 and 4,327,100) have been shown to possess inotropic and anticoagulant activity. U.S. Pat. Nos. 4,299,834 and 4,353,909 describe similarly substituted purine and 6-hydroxy-imidazo[4,5-b]pyridine derivatives. The analogous imidazo[4,5-c]pyridine derivatives have also been taught to be inotropic agents. See, e.g., European Patent Application Nos. 72,926 and 79,083 and British Patent Application No. 2,119,377.

Certain 3-alkyl-2-phenylimidazo[1,2-a]pyrimidines are taught in French Pat. No. 2,510,576 to be anti-inflammatory agents. Certain imidazo-pyridines and -pyrazines and their 5,6,7,8-tetrahydro analogs are taught to be anti-secretory agents in European Patent Application Nos. 33,094 and 68,378. 2-Phenyl-5,6,7,8-tetrahydroimidazo[1,2-a]pyridine is taught in *J. Chem. Soc. (C)*, 3280 (1971); no pharmaceutical utility is disclosed.

The present invention provides for a series of novel phenylimidazole compounds, their formulations and their use as orally effective positive inotropic agents which have minimal effects on blood pressure and heart rate. The compounds also possess vasodilitation activity.

SUMMARY OF THE INVENTION

This invention provides for pharmaceutically useful compounds having the formula

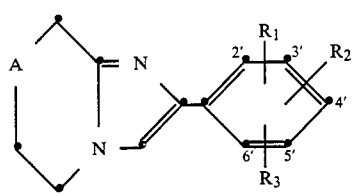

and their pharmaceutically acceptable salts, wherein:
A is $CH_2$ or NH;
each of $R_1$ and $R_2$ is independently hydrogen, $C_1-C_4$ alkyl, $C_1-C_4$ alkoxy, allyloxy, propargyloxy, benzyloxy, ($C_1-C_4$ alkyl)thio, ($C_1-C_4$ alkyl)sulfinyl, ($C_1-C_4$ alkyl)sulfonyl, hydroxy, halo, cyano, nitro, amino, mono- or di-($C_1-C_4$ alkyl)amino, trifluoromethyl, or Z-Q-substituted $C_1-C_4$ alkoxy, wherein Q is oxygen, sulfur, sulfinyl, sulfonyl, or a bond, and Z is $C_1-C_4$ alkyl, phenyl or phenyl substituted with halo, $C_1-C_4$ alkyl, $C_1-C_4$ alkoxy, hydroxy, nitro, amino, ($C_1-C_4$ alkyl)thio, ($C_1-C_4$ alkyl)sulfinyl, or ($C_1-C_4$ alkyl)sulfonyl; and
$R_3$ is hydrogen, $C_1-C_4$ alkoxy, $C_1-C_4$ alkyl, or halo; with the proviso that $R_1$, $R_2$, and $R_3$ may not all be hydrogen at the same time.

In addition to the compounds of formula I, this invention also provides a method of treating a mammal, including a human, suffering from or susceptible to the conditions of hypertension or heart failure, which comprises administering to said mammal an effective amount of a compound of formula I.

According to a further aspect of the present invention there is provided a pharmaceutical formulation which comprises as active ingredient a compound of Formula I as defined above, associated with a pharmaceutically acceptable carrier therefor.

DETAILED DESCRIPTION AND PREFERRED EMBODIMENT

The compounds of this invention where A is NH are referred to as 5,6,7,8-tetrahydro-2-phenylimidazo[1,2-a]pyrazines and where A is $CH_2$, the compounds are 5,6,7,8-tetrahydro-2-phenylimidazo[1,2-a]pyridines.

A preferred group of compounds are those which have two substituents on the phenyl ring, especially those selected from $C_1-C_4$ alkyl, $C_1-C_4$ alkoxy, halogen, ($C_1-C_4$ alkyl)thio, ($C_1-C_4$ alkyl)sulfinyl, ($C_1-C_4$ alkyl)sulfonyl, trifluoromethyl, or Z-Q-substituted $C_1-C_4$ alkoxy, and pharmaceutically acceptable salts thereof.

Preferred groups of compounds are those compounds wherein the substituents are at the 3'- and 4'-, and especially the 2'- and 4'-positions of the phenyl ring.

Especially preferred groups as defined above are those where "$C_1-C_4$ alkyl" is methyl, "($C_1-C_4$ alkyl)sulfinyl" is methylsulfinyl, "($C_1-C_4$ alkyl)sulfonyl" is methylsulfonyl, and "$C_1-C_4$ alkoxy" is methoxy. Preferred Z-Q-substituted $C_1-C_4$ alkoxy compounds are those wherein $C_1-C_4$ alkoxy is ethoxy or n-propoxy, Q is oxygen, sulfur, sulfinyl, or sulfonyl, and Z is $C_1-C_4$ alkyl, phenyl or phenyl substituted with halo, $C_1-C_4$ alkoxy, or hydroxy. Compounds substituted at the 2'-position of the phenyl ring with $C_1-C_4$ alkoxy, especially methoxy, or with the preferred Z-Q-substituted $C_1-C_4$ alkoxy substituents, and at the 4'-position of the phenyl ring with trifluoromethyl, $C_1-C_4$ alkoxy, ($C_1-C_4$ alkyl)sulfinyl, or ($C_1-C_4$ alkyl)sulfonyl are particularly preferred, with 2',4'-dimethoxyphenyl, 2'-methoxy-4'-trifluoromethylphenyl, 2'-methoxy-4'-methylsulfinylphenyl, and 2'-methoxy-4'-methylsulfonylphenyl groups being most preferred.

The following definitions refer to the various terms used throughout this disclosure.

The term "halo" refers to fluoro, chloro, bromo, or iodo.

The term "$C_1-C_4$ alkyl" refers to the straight and branched aliphatic radicals of one to four carbon atoms including methyl, ethyl, propyl, isopropyl, butyl, isobutyl, sec-butyl, and tert-butyl.

The term "$C_1-C_4$ alkoxy" includes the straight and branched aliphatic ether radicals of one to four carbon atoms such as methoxy, ethoxy, propoxy, isopropoxy, butoxy, isobutoxy, sec-butoxy, and tert-butoxy.

The compounds of this invention as represented by Formula I may be prepared by any of several methods known in the art.

One method of preparation consists of the reaction of an amine of the formula II

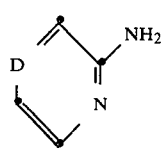

where D is N or CH, with an α-haloketone of the formula

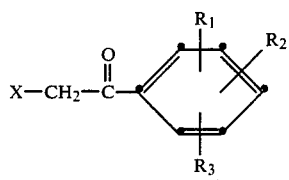

wherein $R_1$, $R_2$, and $R_3$ are as defined above and X is halo, preferably bromo or chloro, to provide an intermediate of the formula IV.

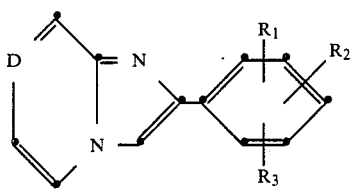

The reaction may be performed in the absence of a solvent, but is generally carried out in a suitable nonreactive solvent, such as dimethylformamide, benzene, toluene, xylene, ethylene glycol, pyridine, acetone, and the like. Temperatures in the range of −20° C. to 250° C. may be employed with a preferred range of 20°–60° C. See generally the preparations taught in U.S. Pat. No. 4,177,274 (imidazo[1,2-a]pyridines) and French Pat. No. 2,510,576 (2-phenylimidazo[1,2-a]pyrimidines).

An alternate procedure consists of the reaction as described above wherein the amine intermediate is similar to II except that one of the carbon atoms adjacent to D when D is N is now CX, preferably CCl, instead of CH. This halo-substituted heterocyclic amine (II') may be used in place of II in the reaction with III to provide the corresponding halo-substituted intermediates (referred to as IV'). The advantage in using the halo-substituted heterocyclic amine II' is found in the relative increased reactivity of the amine which provides the intermediates IV' in greater yields and purity.

The intermediates IV or IV' are then transformed into the desired compounds I by catalytic hydro genation, such as reacting IV or IV' with hydrogen in an inert solvent in the presence of a catalyst, such as palladium-on-carbon or palladium-on-barium sulfate. An acid scavenger, such as a trialkylamine, may be added to form a salt with the hydrohalide acid formed as a by-product when IV' is used.

An alternate method of preparing compounds I consists of the reaction of an imine of the formula V

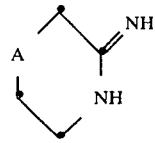

with intermediate III to give compounds I directly. In this reaction, the imine, usually as the hydrohalide salt, and III are heated together in approximately equimolar amounts preferably in a high boiling nonreactive solvent such as dimethylformamide or dioxane at temperatures from about 35° C. up to the reflux temperature of the reaction mixture. After removal of the solvent, the desired product I can be purified by the usual methods of chromatography and/or crystallization.

The amine starting materials II and II' are commercially available or may be prepared by published methods from available starting materials by the proper sequence of nitrations, reductions, acylations, hydrolyses, halogenations, or aminations. The required α-haloketones of Formula III and imines V are either commercially available, are known in the literature, or are prepared by published methods or by methods described herein.

The sulfinyl and sulfonyl derivatives of this invention may be prepared directly by the reactions described above using the corresponding sulfinyl or sulfonyl intermediates III, or by oxidation of the corresponding mercapto compounds of Formula I by methods known in the art. One or two equivalents, respectively, of hydrogen peroxide in an alcohol, a peracid, such as meta-chloroperbenzoic acid in methylene chloride, or similar oxidants may be used to effect these transformations.

In addition, some of the compounds of Formula I may be prepared by subsequent derivatizations of other compounds of Formula I by methods known in the art. Thus, amine compounds of Formula I may be prepared from corresponding halo derivatives, hydroxy substituents may be selectively alkylated, and like transformations.

Illustrative of the compounds of this invention are the following:

5,6,7,8-tetrahydro-2-[2-(β-methylsulfinylethoxy)-4-methoxyphenyl]imidazo[1,2-a]pyrazine, 5,6,7,8-tetrahydro-2-(2-methoxy-4-methylsulfonylphenyl)imidazo[1,2-a]pyridine, 5,6,7,8-tetrahydro-2-[2-methoxy-4-(β-ethylsulfinylethoxy)phenyl]imidazo[1,2-a]pyridine, 5,6,7,8-tetrahydro-2-(2-butoxy-4-methylphenyl)imidazo[1,2-a]pyridine, 5,6,7,8-tetrahydro-2-[2-(β-methylsulfinylethoxy)phenyl]imidazo[1,2-a]pyridine, 5,6,7,8-tetrahydro-2-[2-(β-methylmercaptoethoxy)-5-methylmercaptophenyl]imidazo[1,2-a]pyrazine, 5,6,7,8-tetrahydro-2-[2-(β-ethylsulfinylethoxy)-4-methoxyphenyl]imidazo[1,2-a]pyrazine, 5,6,7,8-tetrahydro-2-(2-methoxy-4-methylsulfinylphenyl)imidazo[1,2-a]pyrazine, 5,6,7,8-tetrahydro-2-(2,4,5-trimethoxyphenyl)imidazo[1,2-a]pyrazine, 5,6,7,8-tetrahydro-2-[2-methoxy-4-(β-methylmercaptoethoxy)phenyl]imidazo[1,2-a]pyridine, 5,6,7,8-tetrahydro-2-(2-fluoro-5-methylsulfinylphenyl)imidazo[1,2-a]pyrazine, 5,6,7,8-tetrahydro-2-(2-ethoxy-4-propylsulfinylphenyl)imidazo[1,2-a]pyrazine,
5,6,7,8-tetrahydro-2-(2-ethoxy-4-ethylsulfonylphenyl)imidazo[1,2-a]pyridine,
5,6,7,8-tetrahydro-2-(4-isopropoxyphenyl)imidazo[1,2-a]pyrazine,
5,6,7,8-tetrahydro-2-(2-β-phenylsulfinylethoxy-4-methoxyphenyl)imidazo[1,2-a]pyrazine,
5,6,7,8-tetrahydro-2-[2,4-bis(methylmercapto)phenyl]imidazo[1,2-a]pyridine,
5,6,7,8-tetrahydro-2-(2-methoxy-4-methylsulfinylphenyl)imidazo[1,2-a]pyridine,
5,6,7,8-tetrahydro-2-[2-(β-ethylmercaptoethoxy)-4-methoxyphenyl]imidazo[1,2-a]pyrazine,
5,6,7,8-tetrahydro-2-(2-methoxy-4-trifluoromethylphenyl)imidazo[1,2-a]pyridine,
5,6,7,8-tetrahydro-2-(4-aminophenyl)imidazo[1,2-a]pyrazine,
5,6,7,8-tetrahydro-2-(2,4-dimethoxyphenyl)imidazo[1,2-a]pyridine,
5,6,7,8-tetrahydro-2-(2,4,6-trimethoxyphenyl)imidazo[1,2-a]pyridine,
5,6,7,8-tetrahydro-2-(2-ethoxy-4-butylsulfonylphenyl)imidazo[1,2-a]pyridine,
5,6,7,8-tetrahydro-2-[2-β-(4-hydroxyphenylsulfinyl)ethoxy-4-methoxyphenyl]imidazo[1,2-a]pyrazine,
5,6,7,8-tetrahydro-2-(2-fluoro-4-methoxyphenyl)imidazo[1,2-a]pyrazine,
5,6,7,8-tetrahydro-2-(2-methoxy-4-methylsulfonylphenyl)imidazo[1,2-a]pyrazine,
5,6,7,8-tetrahydro-2-(2-methoxy-4-methylsulfonylphenyl)imidazo[1,2-a]pyridine,
5,6,7,8-tetrahydro-2-(2-methoxy-4-methylmercaptophenyl)imidazo[1,2-a]pyridine,
5,6,7,8-tetrahydro-2-(2-allyloxy-4-methoxyphenyl)imidazo[1,2-a]pyrazine,
5,6,7,8-tetrahydro-2-(2-methoxyphenyl)imidazo[1,2-a]pyridine,
5,6,7,8-tetrahydro-2-(2-fluoro-4-methylsulfinylphenyl)imidazo[1,2-a]pyrazine,
5,6,7,8-tetrahydro-2-(3-butyl-4-methoxyphenyl)imidazo[1,2-a]pyridine,
5,6,7,8-tetrahydro-2-(2-fluoro-5-methylmercaptophenyl)imidazo[1,2-a]pyridine,
5,6,7,8-tetrahydro-2-(4-hydroxyphenyl)imidazo[1,2-a]pyrazine,
5,6,7,8-tetrahydro-2-(2-ethoxy-4-methylphenyl)imidazo[1,2-a]pyrazine,
5,6,7,8-tetrahydro-2-[2-γ-(3,4-dichlorophenoxy)propoxyphenyl]imidazo[1,2-a]pyrazine,
5,6,7,8-tetrahydro-2-(2,4-dimethoxy-3-hydroxyphenyl)imidazo[1,2-a]pyridine,
5,6,7,8-tetrahydro-2-(2,4-dimethoxyphenyl)imidazo[1,2-a]pyrazine,
5,6,7,8-tetrahydro-2-(2-ethoxy-4-propylmercaptophenyl)imidazo[1,2-a]pyridine,
5,6,7,8-tetrahydro-2-(2-fluoro-5-methylsulfonylphenyl)imidazo[1,2-a]pyridine,
5,6,7,8-tetrahydro-2-[2-(γ-ethylsulfinylpropoxy)-4-methoxyphenyl]imidazo[1,2-a]pyrazine,
5,6,7,8-tetrahydro-2-[2-(β-methylsulfinylethoxy)-4-methylsulfinylphenyl]imidazo[1,2-a]pyridine,
5,6,7,8-tetrahydro-2-(3,5-dimethoxyphenyl)imidazo[1,2-a]pyridine,
5,6,7,8-tetrahydro-2-(2-methoxy-4-ethoxyphenyl)imidazo[1,2-a]pyridine,
5,6,7,8-tetrahydro-2-(4-nitro-2-hydroxyphenyl)imidazo[1,2-a]pyrazine,
5,6,7,8-tetrahydro-2-(4-isopropylphenyl)imidazo[1,2-a]pyrazine,
5,6,7,8-tetrahydro-2-(2-β-phenylethoxyphenyl)imidazo[1,2-a]pyridine,
5,6,7,8-tetrahydro-2-(2,4-dihydroxyphenyl)imidazo[1,2-a]pyrazine,
5,6,7,8-tetrahydro-2-[2-methoxy-4-(γ-ethylsulfinylpropoxy)phenyl]imidazo[1,2-a]pyrazine,
5,6,7,8-tetrahydro-2-[2-(γ-ethylmercaptopropoxy)-4-methoxyphenyl]imidazo[1,2-a]pyrazine,
5,6,7,8-tetrahydro-2-(2-methoxy-4-trifluoromethylphenyl)imidazo[1,2-a]pyrazine,
5,6,7,8-tetrahydro-2-(4-dimethylaminophenyl)imidazo[1,2-a]pyridine,
5,6,7,8-tetrahydro-2-(2-methylsulfinylphenyl)imidazo[1,2-a]pyridine,
5,6,7,8-tetrahydro-2-(2-methoxy-4-ethylsulfinylphenyl)imidazo[1,2-a]pyridine,
5,6,7,8-tetrahydro-2-[2-(β-methylsulfinylethoxy)phenyl]imidazo[1,2-a]pyridine,
5,6,7,8-tetrahydro-2-(4-iodophenyl)imidazo[1,2-a]pyrazine,
5,6,7,8-tetrahydro-2-[2-methoxy-4-(β-butylsulfinylethoxy)phenyl]imidazo[1,2-a]pyrazine,
5,6,7,8-tetrahydro-2-(3-isopropoxyphenyl)imidazo[1,2-a]pyrazine,
5,6,7,8-tetrahydro-2-(2-fluoro-4-methylmercaptophenyl)imidazo[1,2-a]pyrazine,
5,6,7,8-tetrahydro-2-(2-methoxy-4-benzyloxyphenyl)imidazo[1,2-a]pyrazine, The pharmaceutically acceptable acid addition salts of this invention include salts derived from inorganic acids such as hydrochloric acid, nitric acid, phosphoric acid, sulfuric acid, hydrobromic acid, hydriodic acid, phosphorous acid and the like, as well as salts derived from nontoxic organic acids such as aliphatic mono- and di-carboxylic acids, phenyl-substituted alkanoic acids, hydroxy-alkanoic and -alkanedioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially the hydrochloride and hydrobromide salt forms.

The compounds may be administered by various routes including the oral, rectal, transdermal, subcutaneous, intravenous, intramuscular, or intranasal routes, being usually employed in the form of a pharmaceutical composition. It is a special feature of these compounds that they are effective positive inotropic agents following oral administration. Such compositions are prepared in a manner well known in the pharmaceutical art and comprise at least one active compound. Accordingly, the invention includes a pharmaceutical composition comprising as active ingredient a compound of Formula I or an acid addition salt thereof, associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate or mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The compositions are preferably formulated in a unit dosage form, each dosage containing from about 5 to 500 mg., more usually about 25 to 300 mg., of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg./kg. of body weight. In the treatment of adult humans, the range of about 1 to 50 mg./kg., in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

In order to more fully illustrate this invention, the following detailed preparations and examples are provided. The examples are illustrative only and are not intended to limit the scope of the invention in any way. The term "m/e" used in characterizing the products refers to the mass-to-charge ratio of ions which appear in the mass spectra of the products. In general, the values correspond to molecular weights of the major peaks, and are so designated "M+."

EXAMPLE 1

5,6,7,8-tetrahydro-2-(2,4-dimethoxyphenyl)imidazo[1,2-a]pyridine

A.

Preparation of α-bromo-2,4-dimethoxyacetophenone

Fifty-three grams of aluminum chloride were added in portions to 55.2 ml. (400 mmoles) of 1,3-dimethoxybenzene and 34.5 ml. (400 mmoles) of bromoacetyl bromide using an external ice-bath to keep the temperature around 0° C. After the aluminum chloride addition was complete, the ice-bath was removed and the reaction mixture was allowed to stir for two hours. The reaction mixture was carefully added to ice water and the resulting mixture extracted with 1500 ml. of ethyl acetate. The organic phase was washed with 500 ml. of 1N hydrochloric acid. The organic phase was separated, dried, and evaporated in vacuo. The residue was separated, dried, and evaporated in vacuo. The residue was crystallized from diethyl ether to give 54.1 g. of the subtitle product as a white crystalline solid.

B.

Preparation of 5,6,7,8-tetrahydro-2-(2,4-dimethoxyphenyl)imidazo[1,2-a]pyridine

A solution of 2.6 g. of 2-iminopiperidine hydrochloride and 5.2 g. of α-bromo-2,4-dimethoxyacetophenone in 20 ml. of dimethylformamide was stirred at room temperature for three hours and overnight at 80° C. The solvent was removed in vacuo and the residue was purified by chromatography over silica gel to provide 540 mg. of the desired product, M+ =258.

Analysis: $C_{15}H_{18}N_2O_2$; Calc.: C, 69.74; H, 7.02; N, 10.84; Found: C, 69.37; H, 6.74; N, 10.52.

EXAMPLE 2

5,6,7,8-tetrahydro-2-(2-methoxy-4-methylsulfonylphenyl)imidazo[1,2-a]pyrazine dihydrochloride

A.

Preparation of 3-fluorophenylacetate

To a solution of 20 ml. of 3-fluorophenol in 200 ml. of dry methylene chloride were added 19.5 ml. of pyridine. The solution was cooled to 0° C. and 17.5 ml. of acetyl chloride were added dropwise with stirring. After the addition was complete, the reaction was stirred for one hour at 0° C. An additional 200 ml. of methylene chloride were added and the organic solution was extracted once with 300 ml. of 1N hydrochloric acid. The organic solution was dried with magnesium sulfate and removed in vacuo to give 34.3 g. of 3-fluorophenylacetate as an oil which was used in the subsequent step without further purification.

B.

Preparation of 2-hydroxy-4-fluoroacetophenone

To a flask containing 34.2 g. of 3-fluorophenylacetate which was cooled to 0° C. were added 40 g. of aluminum chloride in portions. The flask and its contents were allowed to warm to room temperature and the reaction was then placed in an oil bath and heated to 160°–180° C. for two hours. The reaction was cooled to 0° C. and ice was carefully added followed by the addition of 150 ml. of concentrated hydrochloric acid and 250 ml. of ethyl acetate. The mixture was allowed to stir until complete solution occurred. The layers were separated and the ethyl acetate was removed in vacuo. The residue was subjected to steam distillation. The distillate was acidified with 1N hydrochloric acid and extracted with ethyl acetate. The ethyl acetate layer was dried and the solvent was removed in vacuo to give 28 g. of 2-hydroxy-4-fluoroacetophenone as an oil which crystallized on cooling.

C.

Preparation of 2-methoxy-4-fluoroacetophenone

To a solution of 13.9 g. of 2-hydroxy-4-fluoroacetophenone in 75 ml. of dry dimethylformamide were added 30 ml. of methyl iodide. The solution was cooled to 0° C. and 4.1 g. of a 50% oil dispersion of sodium hydride were carefully added. After stirring for one hour at 0° C., the reaction was extracted with ethyl acetate. The organic extract was washed three times with 200 ml. each of 1N hydrochloric acid. The ethyl acetate solution was then dried and removed in vacuo. This reaction and a subsequent identical reaction provided a total of 28 g. of 2-methoxy-4-fluoroacetophenone as an oil which was used in the subsequent step without further purification.

D.

Preparation of 2-methoxy-4-methylmercaptoacetophenone

A suspension of 17 g. of potassium hydroxide in 100 ml. of dry dimethylformamide under a nitrogen atmosphere was cooled to $-10°$ C. with an external ice/acetone bath. To this suspension were added 26 ml. of methanethiol. The reaction mixture was stirred until all the potassium hydroxide was dissolved. At this time, 33.1 g. of 2-methoxy-4-fluoroacetophenone were added and the reaction mixture was stirred for two hours at 0° C. The reaction mixture was poured into 400 ml. of ethyl acetate and the resulting solution was washed three times each with 300 ml. of 1N hydrochloric acid. The organic phase was then dried and evaporated in vacuo to give an oil. Crystallization from 50% ether/hexane afforded 21.3 g. of the desired 2-methoxy-4-methylmercaptoacetophenone.

E.

Preparation of 2-methoxy-4-methylsulfonylacetophenone

To a solution of 3.92 g. of 2-methoxy-4-methylmercaptoacetophenone in 200 ml. of methylene chloride were added 4 g. of m-chloroperbenzoic acid. Thin-layer chromatography indicated the formation of the intermediate sulfoxide derivative. This was followed ten minutes later with a second addition of 4 g. of m-chloroperbenzoic acid. After stirring for one hour, the reaction mixture was washed with 500 ml. of a saturated sodium bicarbonate solution. The organic phase was separated and dried over magnesium sulfate. The organic solution was then evaporated in vacuo to give 3.61 g. of 2-methoxy-4-methylsulfonylacetophenone.

F.

Preparation of α-bromo-2-methoxy-4-methylsulfonylacetophenone

To a suspension of 3.61 g. of 2-methoxy-4-methylsulfonylacetophenone in 100 ml. of acetic acid was added enough methylene chloride to cause solution. While stirring at room temperature, 0.91 ml. of bromine were added. The reaction was stirred until the bromine color was discharged. The reaction was poured into 300 ml. of ethyl acetate and washed twice each with 300 ml. of a saturated sodium chloride solution. The organic solution was further washed with 300 ml. of a saturated sodium bicarbonate solution. The organic phase was dried and the solvent was removed in vacuo. The residual oil crystallized on the addition of diethyl ether giving 4.05 g. of the desired α-bromo-2-methoxy-4-methylsulfonylacetophenone.

Analysis: $C_{10}H_{11}BrSO_4$; Calc.: C, 39.10; H, 3.61; S, 10.44; Br, 26.01; Found: C, 38.92; H, 3.51; S, 10.28; Br, 26.30.

G.

Preparation of 8-chloro-2-(2-methoxy-4-methylsulfonylphenyl)imidazo[1,2-a]pyrazine hydrobromide A suspension of 3.88 g. of 2-amino-3-chloropyrazine and 9.21 g. of α-bromo-2-methoxy-4-methylsulfonylacetophenone in 30 ml. of dimethylformamide was stirred at 40° C. for approximately 60 hours. The resulting precipitate was recovered by filtration affording 2.7 g. of the desired subtitle intermediate. An additional amount of this intermediate was obtained by evaporating the ethyl acetate from the filtrate and heating the filtrate at 50° C. for an additional day providing 1.35 additional grams of the intermediate. Repeating this process one additional day provided another 0.75 g. for a total of 4.8 g. yield.

H.

Preparation of 5,6,7,8-tetrahydro-2-(2-methoxy-4-methylsulfonylphenyl)imidazo[1,2-a]pyrazine dihydrochloride A suspension of 4.5 g. of 8-chloro-2-(2-methoxy-4-methylsulfonylphenyl)imidazo[1,2-a]pyrazine hydrobromide in 190 ml. of dimethylformamide was treated with 3.4 g. of triethylamine and 1 g. of 5% palladium-on-carbon. This mixture was hydrogenated at room temperature at 60 psi for about 75 minutes. The catalyst was removed by filtration and the solvent was removed in vacuo. During the course of solvent removal a precipitate occurred which was removed by filtration. The precipitate was triturated with chloroform and the residue was suspended in methanolic hydrogen chloride. After stirring for a period of time, the methanol was removed by evaporation and the resulting solid was collected with acetone by filtration affording 2.1 g. of the desired title product, $M^+ = 307$.

Analysis: $C_{14}H_{17}N_3O_3S.2HCl$; Calc.: C, 44.22; H, 5.04; N, 11.05; S, 8.43; Cl, 18.65; Found: C, 43.14; H, 5.00; N, 10.65; S, 8.41; Cl, 18.50.

The following formulation examples may employ as active compounds any of the pharmaceutical compounds of the invention.

EXAMPLE 3

Hard gelatin capsules are prepared using the following ingredients:

|  | Quantity (mg./capsule) |
| --- | --- |
| Active compound | 250 |
| Starch dried | 200 |

-continued

| | Quantity (mg./capsule) |
|---|---|
| Magnesium stearate | 10 |

The above ingredients are mixed and filled into hard gelatin capsules in 460 mg. quantities.

EXAMPLE 4

A tablet formula is prepared using the ingredients below:

| | Quantity (mg./tablet) |
|---|---|
| Active compound | 250 |
| Cellulose, microcrystalline | 400 |
| Silicon dioxide, fumed | 20 |
| Stearic acid | 5 |

The components are blended and compressed to form tablets each weighing 665 mg.

EXAMPLE 5

An aerosol solution is prepared containing the following components:

| | Weight % |
|---|---|
| Active ingredient | 0.25 |
| Ethanol | 29.75 |
| Propellant 22 (Chlorodifluoromethane) | 70 |

The active compound is mixed with ethanol and the mixture added to a portion of the propellant 22, cooled to $-30°$ C. and transferred to a filling device. The required amount is then fed to a stainless steel container and diluted with the remainder of the propellant. The valve units are then fitted to the container.

EXAMPLE 6

Tablets each containing 60 mg. of active ingredient are made up as follows:

| | |
|---|---|
| Active ingredient | 60 mg. |
| Starch | 45 mg. |
| Microcrystalline cellulose | 35 mg. |
| Polyvinylpyrrolidone (as 10% solution in water) | 4 mg. |
| Sodium carboxymethyl starch | 0.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 7

Capsules each containing 80 mg. of medicament are made as follows:

| | |
|---|---|
| Active ingredient | 80 mg. |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 8

Suppositories each containing 225 mg. of active ingredient are made as follows:

| | |
|---|---|
| Active ingredient | 225 mg. |
| Saturated fatty acid glycerides to | 2,000 mg. |

The active ingredient is passed through a No. 60 mesh U.S. sieve and suspended in the saturated fatty acid glycerides previously melted using the minimum heat necessary. The mixture is then poured into a suppository mold of nominal 2 g. capacity and allowed to cool.

EXAMPLE 9

Suspensions each containing 50 mg. of medicament per 5 ml. dose are made as follows:

| | |
|---|---|
| Active ingredient | 50 mg. |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

The compounds of this invention and their pharmaceutically acceptable salts have been found to possess useful pharmaceutical properties, including positive inotropy and vasodilation. Certain compounds of the present invention were examined as to their pharmacodynamic effects in the following test systems.

POSITIVE INOTROPIC ACTIVITY IN ISOLATED CAT PAPILLARY MUSCLES

Cats of either sex were anesthetized with Metofane (1,1-difluoro-2,2-dichloroethyl methyl ether, Pittman-Moore) their hearts immediately removed and the papillary muscles dissected and suspended in individual organ baths. A platinum hook secured one end of the muscle to an electrode mounted in the bottom of the bath, and a silk threat attached the tendon to a Statham isometric transducer. The baths contained Krebs-Henseleit solution (36° C., bubbled with 95 percent oxygen-5 percent carbon dioxide) of the following millimolar composition: NaCl, 118; KCl, 4.5; CaCl$_2$, 2.5; KH$_2$PO$_4$, 1.1; MgSO$_4$, 1.2; NaHCO$_3$, 25; and glucose, 11.

A base-line tension of 1.5 g. was applied to each muscle. Square-wave pulses (5.0 msec. in duration, three times threshold voltage) delivered through the hook electrode and a second electrode positioned near the top of the muscle evoked 12 contractions/minute, which were recorded on a Grass polygraph. After the muscles had equilibrated for 60 minutes, the recorder gain was adjusted to that the pen deflected 10 mm. The drug was introduced in a solution of normal saline in an amount to bring the final concentration of the drug to $10^{-5}$ or $10^{-4}$ molar. Increases in contractility were tabulated as millimeters of pen deflection in excess of the baseline value. In each experiment the maximum contractility was measured. Test results are summarized in Table I and are expressed as percent of control (control = 100 percent). Values are the average of results from 2 to 8 muscles.

TABLE I

| Effects of Compounds of Formula I on Contractility in Cat Papillary Muscles | | |
|---|---|---|
| | Contractility of Papillary Muscle* | |
| Compound of | Drug Concentration | |
| Example No. | $10^{-5}$ M | $10^{-4}$ M |
| 1 | 91.5 | 232.0 |
| 2 | 140.5 | 212.0 |

*Data are peak responses at the indicated concentration of drug and are expressed as a percent of control (control = 100 percent).

EXPERIMENTS IN ANESTHETIZED DOGS

Mongrel dogs of either sex ranging in weight from 7 to 14 kg. were used. Anesthesia was induced with sodium pentobarbital (30 mg./kg., i.v.) and maintained with supplemental doses as required. A positive-pressure pump was used to ventilate the dogs through an endotracheal tube (18 strokes/minute, 20 ml./kg. stroke$^{-1}$), and a heating pad kept the body temperature at 37°–38° C.

Femoral arterial blood pressure was measured through a polyethylene catheter filled with heparin solution (16 units/ml.) and connected to a Statham pressure transducer. A strain-gauge arch sutured to the right ventricle of the heart measured cardiac contractility. Tension on the gauge was adjusted to 50 g. and the gain of the recorder (Beckman dynograph) was set so that 50 g. caused a 10-mm. pen deflection; cardiac contractile tension was measured as millimeters of pen deflection or grams of tension. The drug was administered following a 30-45 minute equilibrium period as an i.v. bolus (2–5 ml.) in a normal saline vehicle. In a control experiment, rapid intravenous injection of 50 ml. of 5 percent dextran and mechanical compression of the aorta showed that the contractility measurements were independent of changes in preload and afterload. Heart rate was derived by means of a cardiotach which was triggered by the arterial pressure pulse signal and displayed on the polygraph. The maximum effects on contractility at various dose levels were calculated as a percent of control (control = 100 percent). The compound of Example 2 produced an ED$_{50}$ (dose, i.v., which produced a peak increase of 50% over control) of 0.6 mg./kg.

I claim:

1. A compound of the formula

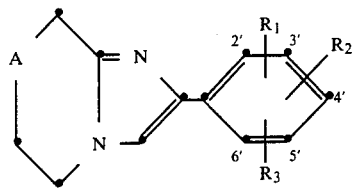

and their pharmaceutically acceptable salts, wherein:
A is CH$_2$;
each of R$_1$ and R$_2$ is independently hydrogen, C$_1$–C$_4$ alkyl, C$_1$–C$_4$ alkoxy, allyloxy, propargyloxy, benzyloxy, (C$_1$–C$_4$ alkyl)thio, (C$_1$–C$_4$ alkyl)sulfinyl, (C$_1$–C$_4$ alkyl)sulfonyl, hydroxy, halo, cyano, nitro, mono- or di-(C$_1$–C$_4$ alkyl)amino, trifluoromethyl, or Z-Q-substituted C$_1$–C$_4$ alkoxy, wherein Q is oxygen, sulfur, sulfinyl, sulfonyl, or a bond, and Z is C$_1$–C$_4$ alkyl, phenyl or phenyl substituted with halo, C$_1$–C$_4$ alkyl, C$_1$–C$_4$ alkoxy, hydroxy, nitro, amino, (C$_1$–C$_4$ alkyl)thio, (C$_1$–C$_4$ alkyl)sulfinyl, or (C$_1$–C$_4$ alkyl)sulfonyl;
and R$_3$ is hydrogen, C$_1$–C$_4$ alkoxy, C$_1$–C$_4$ alkyl, or halo;
with the proviso that R$_1$, R$_2$, and R$_3$ may not all be hydrogen at the same time.

2. The compounds of claim 1 wherein R$_1$ is methoxy.

3. The compounds of claim 2 wherein R$_1$ is at the 2'-position.

4. The compounds of claim 3 wherein R$_2$ is methylsulfinyl.

5. The compounds of claim 3 wherein R$_2$ is methoxy.

6. The compounds of claim 3 wherein R$_2$ is methylmercapto.

7. The compounds of claim 3 wherein R$_2$ is methylsulfonyl.

8. The compound of claim 5 which is 5,6,7,8-tetrahydro-2-(2,4-dimethoxyphenyl)imidazo[1,2-a]pyridine or a pharmaceutically acceptable salt thereof.

9. A method of producing a positive inotropic effect in a mammal, which comprises administering to such mammal an effective amount of a compound of claim 1.

10. A method according to claim 9 wherein R$_1$ is methoxy at the 2'-position and R$_2$ is methoxy, methylsulfinyl, or methylsulfonyl at the 4'-position.

11. The method of claim 10 wherein the compound is 5,6,7,8-tetrahydro-2-(2,4-dimethoxyphenyl)imidazo[1,2-a]pyridine or a pharmaceutically acceptable salt thereof.

12. A pharmaceutical formulation useful for producing a positive inotropic effect in a mammal comprising an effective amount of a compound of claim 1 in association with a pharmaceutically acceptable carrier or diluent.

13. The formulation of claim 12 wherein the compound is 5,6,7,8-tetrahydro-2-(2,4-dimethoxyphenyl)imidazo[1,2-a]pyridine or a pharmaceutically acceptable salt thereof.

* * * * *